US012565788B2

(12) United States Patent
Zhong et al.

(10) Patent No.: US 12,565,788 B2
(45) Date of Patent: Mar. 3, 2026

(54) UNDERWATER GERMICIDAL LAMP ASSEMBLY AND POOL-CLEANING ROBOT

(71) Applicant: Chasing-Innovation Technology Co., Ltd., Shenzhen (CN)

(72) Inventors: Guofeng Zhong, Shenzhen (CN); Changgen Zhou, Shenzhen (CN); Xun Zhang, Shenzhen (CN)

(73) Assignee: Chasing-Innovation Technology Co., Ltd., Shenzhen (CN)

( * ) Notice: Subject to any disclaimer, the term of this patent is extended or adjusted under 35 U.S.C. 154(b) by 0 days.

(21) Appl. No.: 19/072,970

(22) Filed: Mar. 6, 2025

(65) Prior Publication Data

US 2025/0320740 A1     Oct. 16, 2025

Related U.S. Application Data

(63) Continuation of application No. PCT/CN2025/071268, filed on Jan. 8, 2025.

(30) Foreign Application Priority Data

Apr. 16, 2024    (CN) .......................... 202420789072.8

(51) Int. Cl.
*E04H 4/16*          (2006.01)
*A61L 2/10*          (2006.01)

(52) U.S. Cl.
CPC .............. *E04H 4/1654* (2013.01); *A61L 2/10* (2013.01); *A61L 2202/11* (2013.01); *A61L 2202/20* (2013.01)

(58) Field of Classification Search
CPC .... C02F 1/325; C02F 1/32; C02F 2201/3222; C02F 2201/3223; C02F 2201/3228;
(Continued)

(56) References Cited

U.S. PATENT DOCUMENTS

| | | | |
|---|---|---|---|
| 7,081,225 B1 * | 7/2006 | Hollander | ............... C02F 1/325 |
| | | | 313/635 |
| 2009/0232701 A1 * | 9/2009 | Porat | ..................... E04H 4/1654 |
| | | | 422/186.3 |
| 2014/0166045 A1 * | 6/2014 | Herring | ................. E04H 4/1654 |
| | | | 134/1 |

FOREIGN PATENT DOCUMENTS

| | | |
|---|---|---|
| CN | 101939261 A | 1/2011 |
| CN | 112942918 A | 6/2021 |

(Continued)

OTHER PUBLICATIONS

Jiang et al., English machine translation CN 219604976 U, pp. 1-5 (Year: 2023).*

(Continued)

*Primary Examiner* — Claire A Norris
(74) *Attorney, Agent, or Firm* — Andrew C Cheng

(57)          ABSTRACT

The present disclosure discloses a pool-cleaning robot including a housing defining a receiving chamber therein, a power assembly, an underwater germicidal lamp assembly, a filter assembly, and a pump assembly. The housing defines a water inlet and a water outlet which are fluidly communicated with one another. The pump assembly is configured to drive the water flowing into the receiving chamber and being filtered by the filter assembly. The underwater germicidal lamp assembly includes a base, a light source module, and a lamp cover. The light source module includes a light-emitting element. An area of the lamp cover corresponding to a light-emitting area of the light source module is a light-transmitting area. A light-emitting surface of the light-transmitting area is provided with a laminating film. The present disclosure further discloses the above described underwater germicidal lamp assembly.

18 Claims, 12 Drawing Sheets

100

(58) Field of Classification Search
    CPC ...... E04H 4/1654; A61L 2/10; A61L 2202/11;
                                                A61L 2202/20
    USPC ........................................... 210/748.1, 167.1
    See application file for complete search history.

(56) References Cited

FOREIGN PATENT DOCUMENTS

| CN | 219604976 U | * | 8/2023 |
| CN | 118327359 A |   | 7/2024 |
| KR | 101142520 B1 | * | 5/2012 |

OTHER PUBLICATIONS

KR 101142520 B1, English machine translation, pp. 1-7 (Year: 2012).*
International Search Report Dated Apr. 17, 2025 for Corresponding PCT Application No. PCT/CN2025/071268.
Written Opinion of the International Searching Authority Dated Apr. 17, 2025 for Corresponding PCT Application No. PCT/CN2025/071268.

* cited by examiner

100

100

619
661
617
615
613
616
612
614
611

Release film
Pressure-sensitive adhesive
ETFE base film

626

UNDERWATER GERMICIDAL LAMP ASSEMBLY AND POOL-CLEANING ROBOT

CROSS-REFERENCE TO RELATED APPLICATIONS

The present application is a Continuation Application of PCT Application No. PCT/CN2025/071268, filed on Jan. 8, 2025, which claims the priority of Chinese Patent Application No. 202420789072.8, filed on Apr. 16, 2024, the entire contents of which are hereby incorporated by reference.

TECHNICAL FIELD

The present disclosure relates to the field of germicidal lamp assembly technology, specifically to an underwater germicidal lamp assembly and a pool-cleaning robot having the underwater germicidal lamp assembly.

DESCRIPTION OF THE PRIOR ART

With the development of robot technology for cleaning pools, the market has also placed heightened demands on it. For example, the germicidal lamps installed at the outlet or on the outer wall of the bottom of the robot body can not only achieve the objective of filtering and cleaning the pool water, but also sterilize and disinfect the pool water or pool walls. However, after used for a period of time, a light transmittance of existing germicidal lamps decreases, which affects the germicidal effect. Eventually, unpleasant odors are generated due to the presence of large quantities of bacteria, thereby affecting the customer experience.

SUMMARY OF THE DISCLOSURE

Based on the above, the present disclosure provides the following technical solution: The first aspect of the present disclosure provides an underwater germicidal lamp assembly which includes a base, a light source module connected to the base and a lamp cover covering the light source module. The light source module includes a light-emitting element. An area of the lamp cover corresponding to a light-emitting area of the light source module being a light-transmitting area. Wherein a light-emitting surface of the light-transmitting area is provided with a laminating film.

In some embodiments, the laminating film is a removable laminating film; or the laminating film is permanently attached on the light emitting surface of the light-transmitting area.

In some embodiments, the light-transmitting area is made of glass.

In some embodiments, the glass is quartz glass.

In some embodiments, the light source module further includes a substrate, the light-emitting element is a plurality of lamp beads disposed on the substrate.

In some embodiments, the light-emitting element includes a fluorescent tube.

In some embodiments, the light-transmitting area of the lamp cover is concave relative to an outer surface of the lamp cover.

In some embodiments, wherein the base has opposite first and second sides, the light source module is disposed on the first side of the base, and a plurality of heat-dissipating fins are disposed on the second side of the base.

In some embodiments, an accommodation cavity is formed on a side of the base disposing the light source module, the light source module is received in the accommodation cavity, and the lamp cover is connected to the base in a sealed manner thereby sealing the accommodation cavity.

In some embodiments, the lamp cover is snapped on a periphery of the base, or the lamp cover and the base are connected by a fastener.

The second aspect of this disclosure further discloses a pool-cleaning robot, which includes a housing, defining a receiving chamber therein, a power assembly, connected to the housing, an underwater germicidal lamp assembly, as well as a filter assembly and a pump assembly arranged in the receiving chamber. The housing defines a water inlet and a water outlet which are fluidly communicated with one another. The power assembly is connected to the housing and configured to provide power to drive the pool-cleaning robot to travel in a pool. The filter assembly is arranged in the receiving chamber and having a filter chamber that is in fluid communication with the water inlet and the water outlet. The pump assembly is arranged in the receiving chamber and configured to drive the water flowing into the receiving chamber from the water inlet and then out from the water outlet after being filtered by the filter assembly. The underwater germicidal lamp assembly includes a base; a light source module connected to the base; and a lamp cover covering the light source module. The light source module includes a light-emitting element. An area of the lamp cover corresponding to a light-emitting area of the light source module is a light-transmitting area. Wherein a light-emitting surface of the light-transmitting area is provided with a laminating film.

In some embodiments, the germicidal lamp assembly is arranged on an outer wall of the housing or inside the housing.

In some embodiments, the germicidal lamp assembly is arranged in the receiving chamber, and located above, below and/or at a side of the filter assembly.

In some embodiments, the germicidal lamp assembly is arranged on a side wall of the flow channel of the water inlet to irradiate the flow channel of the water inlet.

In some embodiments, a shape of the germicidal lamp assembly is substantially adapted to a shape of the water inlet.

In some embodiments, wherein the laminating film contains material of ETFE or FEP.

In some embodiments, the laminating film is a removable laminating film; or the laminating film is permanently attached on the light emitting surface of the light-transmitting area.

In some embodiments, the light source module further comprises a substrate, and the light-emitting element is a plurality of lamp beads disposed on the substrate; or the light-emitting element includes a fluorescent tube.

In some embodiments, the light-transmitting area of the lamp cover is recessed inwardly relative to an outer surface of the lamp cover.

In the prior art, a surface of the lamp cover of the underwater germicidal lamp hardens and adsorbs a layer of impurities due to long-term operation, thus affecting a light transmittance and germicidal efficiency. Compared with the prior art, in the underwater germicidal lamp according to embodiments of the present disclosure, the light-emitting surface of the light-transmitting area is equipped with the laminating film. The laminating film may reduce the problem of the impurities directly attaching on a surface of the lamp cover, thus avoiding decreasing a light transmittance caused by chemical reactions between the lamp cover and impurities. In this way, the light transmission variation in the light-transmitting area of the lamp cover can be reduced, thus ensuring the germicidal effect.

BRIEF DESCRIPTION OF DRAWINGS

To illustrate the technical solution of the embodiments of the present disclosure more clearly, the drawings used in embodiments or the prior art are briefly described below. Apparently, the drawings in the following description are some embodiments of the present disclosure, and according to these drawings, an ordinary skilled person in the art can obtain other drawings without paying any creative effort.

DESCRIPTION OF EMBODIMENTS

Figure 1:
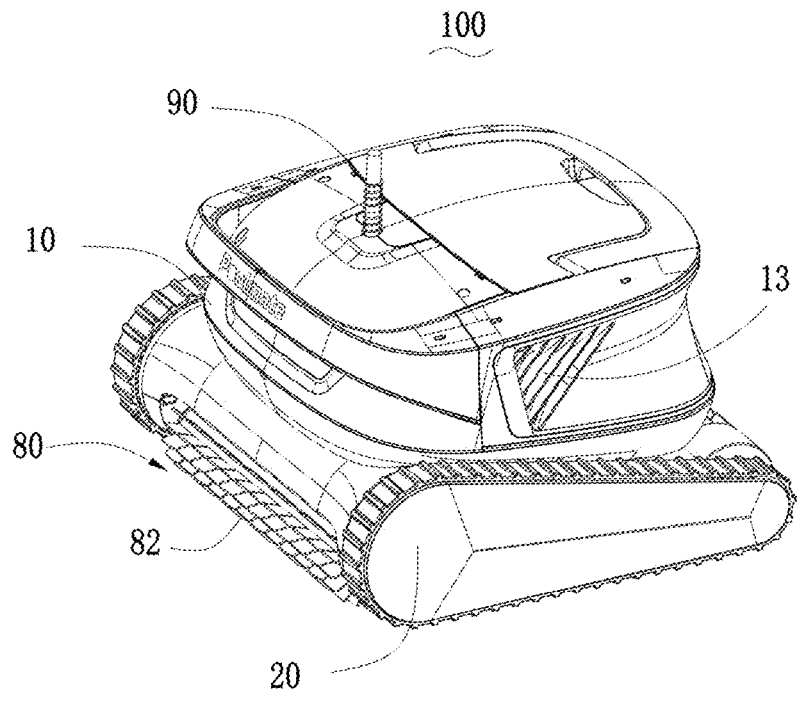
FIG. 1 is a perspective view of a pool-cleaning robot according to a first embodiment of the present disclosure.
Figure 2:
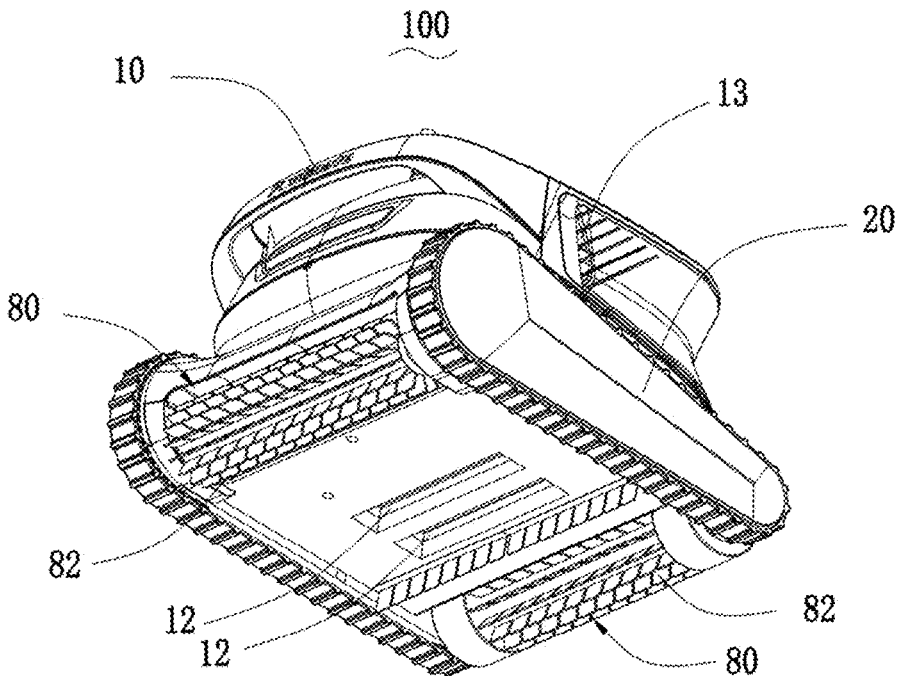
FIG. 2 is a perspective view of the pool-cleaning robot shown in FIG. 1 viewed from another angle.
Figure 3:
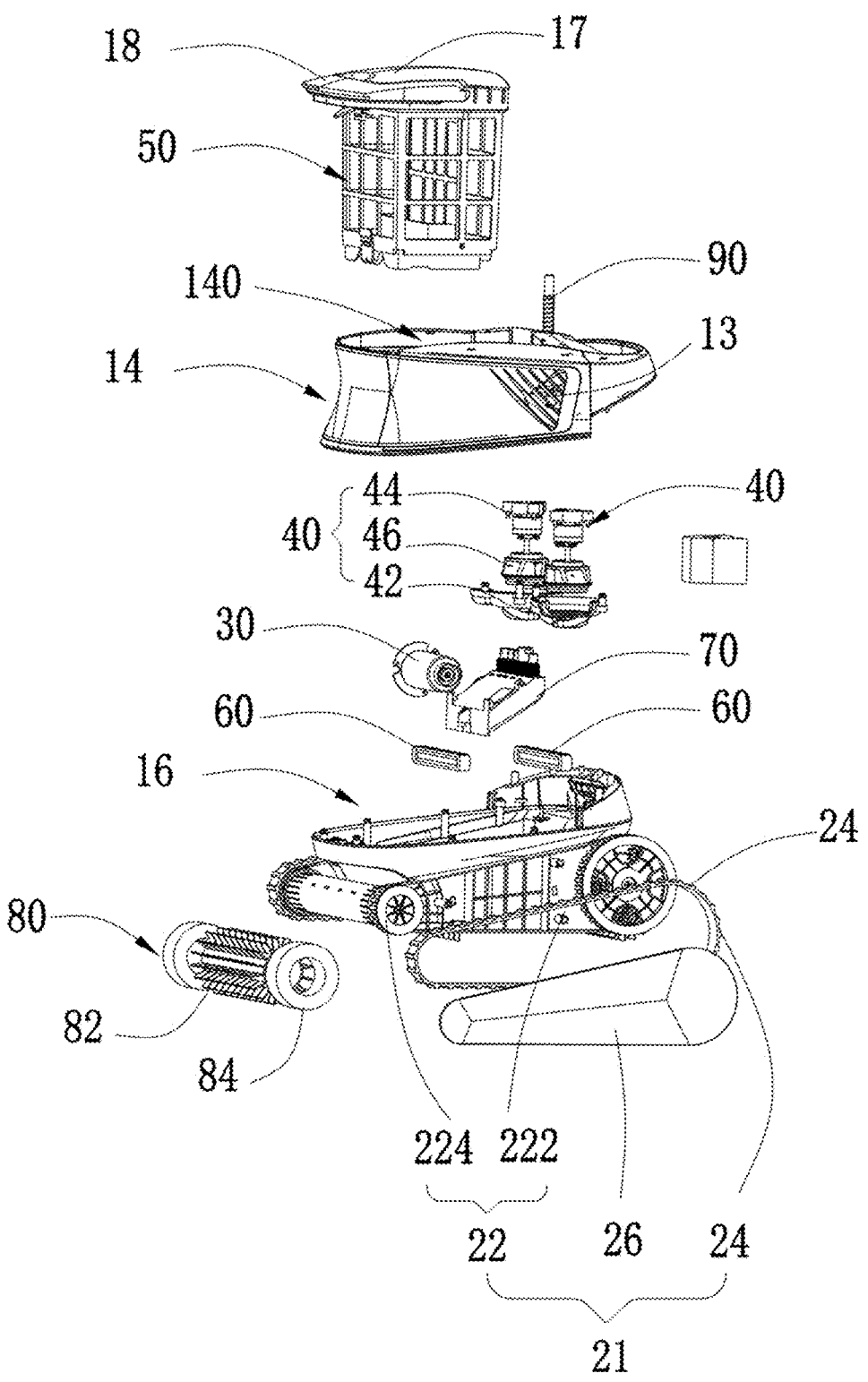
FIG. 3 is a three-dimensional exploded view of the pool-cleaning robot shown in FIG. 1.

In order to make the technical problems, solutions, and beneficial effects to be solved in the present application clearer, the following is a further detailed explanation of the present application in conjunction with the accompanying drawings and embodiments. It should be understood that the specific embodiments described here are only used to explain the present application and are not intended to limit it.

It should be noted that when a component is referred to as "fixed to" or "set to" other component, it can be directly or indirectly on the other component. When a component is referred to as "connected to" other component, it can be directly or indirectly connected to the other component.

It should be understood that the terms "length", "width", "up", "down", "front", "back", "left", "right", "vertical", "horizontal", "top", "bottom", "inside", "outside", and other indications of orientation or positional relationships are based on the orientation or positional relationships shown in the accompanying drawings, and are only for the convenience of describing the present application and simplifying the description, rather than indicating or implying that a device or component referred to must have a specific orientation, be constructed and operated in a specific orientation, it cannot be understood as a limitation of the present application.

Herein "inside" refers to the side closer to the center of the corresponding component or the center of the entire device, and "outside" refers to the side away from the center of the corresponding component or the center of the entire device.

In addition, the description of "first", "second" etc. in the present application is used for descriptive purpose only and is not to be understood as indicating or imply their relative importance or implicitly indicate the number of indicated technical features. Thus, features defined with "first", "second" may explicitly or implicitly include at least one such feature. In the description of the present application, "multiple" means two or more, unless otherwise specified.

FIGS. 1-8 show a pool-cleaning robot 100 according to a first embodiment of the present disclosure, which includes a housing 10 with a receiving chamber 11, a power assembly 20 connected to the housing 10, a germicidal lamp assembly 60, a pump assembly 40, and a filter assembly 50. The pump assembly 40 and the filter assembly 50 are installed in the receiving chamber 11.

The power assembly 20 is configured to provide power to drive the pool-cleaning robot 100 to travel in the pool. In this embodiment, the power assembly 20 includes a walking assembly 21 and a driving assembly 30. The drive assembly 30 may include a drive motor and a reduction gearbox. The walking assembly 21 includes a wheelset 22, and the driving assembly 30 is in transmission connection with the wheelset 22 for driving the wheelset 22 to rotate, thereby driving the pool-cleaning robot 100 to move or turn in the pool.

The housing 10 defines a water inlet 12 and a water outlet 13. The germicidal lamp assembly 60 is arranged at the water inlet 12. The germicidal lamp assembly 60 includes a UV germicidal lamp, preferably a UV-C germicidal lamp, that is, the ultraviolet wavelength of the germicidal lamp is in a range of 200-280 nm, preferably 240-270 nm. Ultraviolet within this wavelength range has a powerful disinfection effect, and it can directly damage the DNA and RNA of cells and viruses, leading to their rapid death. Additionally, it effectively decomposes ozone in water. Of course, the germicidal lamp assembly 50 may also include other germicidal lamps suitable for underwater work.

Specifically, the germicidal lamp assembly 60 of this embodiment is disposed on an inner wall of one side of the water inlet 12 and extends along a length direction thereof. Preferably an entire flow channel of the water inlet 12 is located within an irradiation range of the germicidal lamp assembly 60. The germicidal lamp assembly 60 of this embodiment is arranged on a side wall of the flow channel of the water inlet 12 to directly sterilize the water entering the water inlet 12, effectively reducing the number of bacteria entering the filter assembly 50.

Preferably, the water inlet 12 is in a long strip shape, and the germicidal lamp assembly 60 is in a long strip shape, too. A length of the germicidal lamp assembly 60 is approximately equal to that of the water inlet 12, to fully increase the irradiation range of the water inlet 12 and improve the germicidal effect. It is understood that in other embodiments, the water inlet 12 may also be configured in other shapes, such as an arc or a circle. Correspondingly, the germicidal lamp assembly 60 is also preferably configured in an arc or annular shape matching the water inlet, so as to maximize the irradiation to the flow channel of the water inlet 12 and ensure the germicidal effect.

Figures 4, 5:
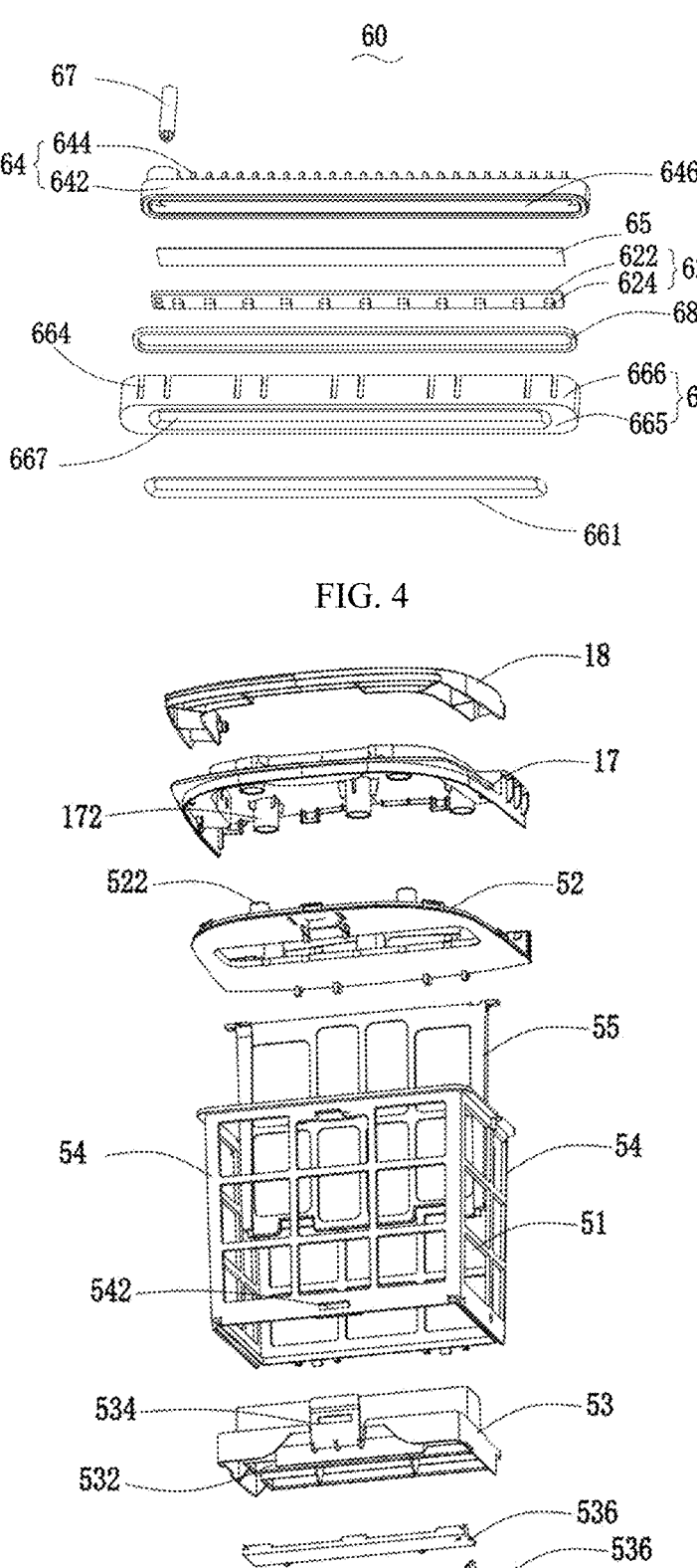
FIG. 4 is a three-dimensional exploded view of a germicidal lamp assembly of the pool-cleaning robot shown in FIG. 3.
FIG. 5 is an exploded perspective view of a filter assembly of the pool-cleaning robot shown in FIG. 3.
Figure 6:
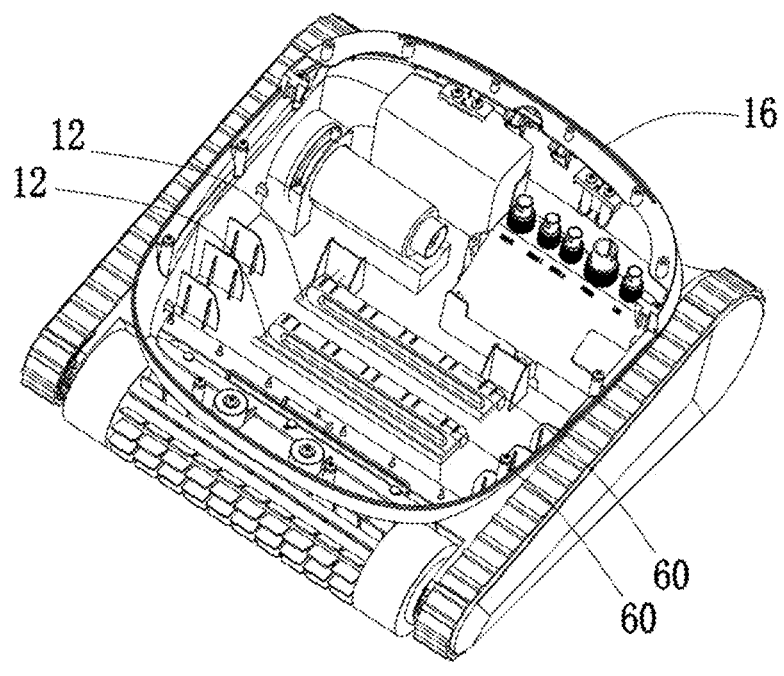
FIG. 6 is a perspective view of a lower housing of the pool-cleaning robot shown in FIG. 1.
Figure 7:
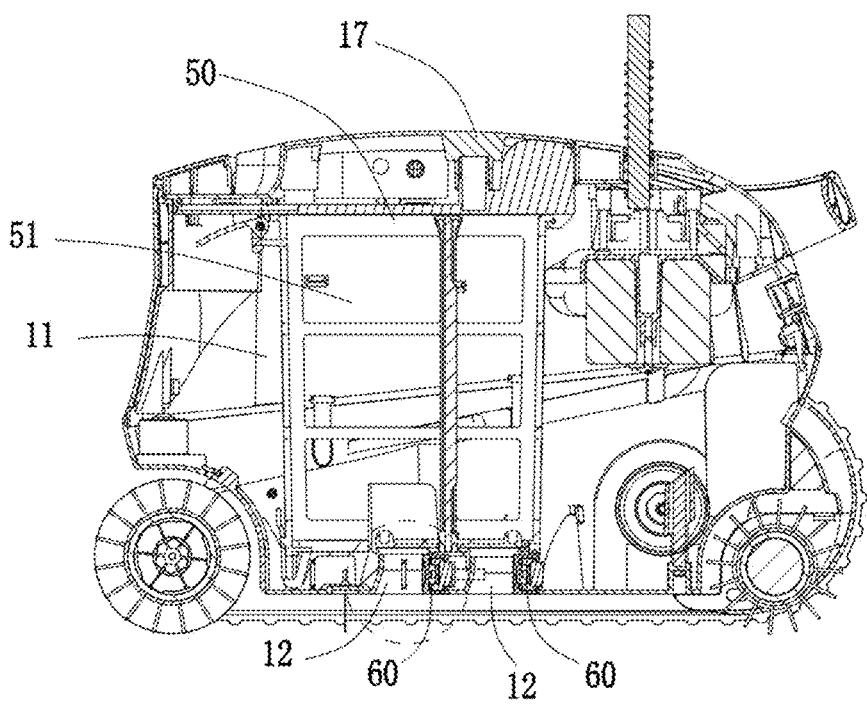
FIG. 7 is a cross-sectional view of the pool-cleaning robot shown in FIG. 1.

As shown in FIG. 4, specifically, the germicidal lamp assembly 60 includes a light source module 62, a heat-dissipating seat 64 and a lamp cover 66. The heat-dissipating seat 64 includes a base 642 and a plurality of heat-dissipating fins 644 disposed on an upper side surface of the base 642. The light source module 62 is fixed on a lower side of the base 642 of the heat-dissipating seat 64. The light source module 62 includes a light-emitting element.

In one embodiment, the light source module 62 includes a substrate 622 and a plurality of lamp beads 624 disposed on the substrate 622. The lamp beads 624 serves as the light-emitting element for emitting Ultraviolet rays. Referring to FIG. 4, in this embodiment, the lamp beads 624 are arranged in a straight line along the substrate 622. It is understood that the arrangement of the lamp beads 624 is not limited to this. The substrate 622 is attached to a lower surface of the base 642. The lamp beads 624 are disposed on a side of the substrate 622 facing away from the base 642. Connecting surfaces between the substrate 622 and the base 642 are preferably coated with thermal conductive paste 65, which is beneficial for quickly conducting the heat from the substrate 622 to the base 642 of the heat-dissipating seat 64, and then dissipating the heat through the heat-dissipating fins 644. The heat-dissipating seat 64 is preferably made of a metal material with good thermal conductivity, such as aluminum or copper, etc.

The lamp cover 66 is connected to the base 642 of the heat-dissipating seat 64 for covering the light source module 62 inside to protect a circuit of the light source module 62. Preferably, a sealing ring 68 is provided between the lamp cover 66 and the lower surface of the base 642 to seal the light source module 62 and prevent water seepage from damaging the circuit of the light source module 62 during underwater operation.

Preferably, a bottom surface of the base 642 is recessed inwardly to form an accommodation cavity 646, and the light source module 62 is received in the accommodation cavity 646. The lamp cover 66 is connected to the base 642 in a sealed manner, thereby enclosing the accommodating cavity 646 of the base 642, as well as sealing the accommodating chamber 646 by means of the sealing ring 68.

In this embodiment, the lamp cover 66 is snapped on a periphery of the base 624 of the heat-dissipating seat 64, and is preferably tightly fitted. Specifically, the lamp cover 66 includes an end wall 665 and a side wall 666 extending from a periphery of the end wall 665. To facilitate assembly, a plurality of slits 664 are defined on a perimeter of the lamp cover 66. The configuration of the slits 664 facilitates the deformation of the perimeter of the lamp cover 66 to expand slightly outwardly during assembly so that it is easily sleeved onto the periphery of the base 624.

Figure 17:
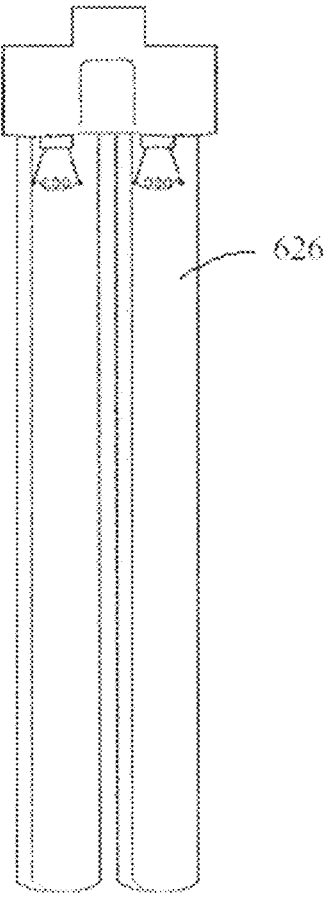
FIG. 17 is a schematic view of a light source module according to another embodiment in FIG. 8.

In another embodiment, the light-emitting element may be a fluorescent tube. Referring to FIG. 17, a fluorescent tube 626 may serve as the light-emitting element to replace the lamp beads of the light source module 62 in FIG. 8.

Preferably, an area of the lamp cover 66 corresponding to a light-emitting area of the light source module 62 is a light-transmitting area 667. Specifically, an area of the lamp cover 66 corresponding to the lamp beads 624 of the light source module 62 is the light-transmitting area 667; or an area of the lamp cover 66 corresponding to the fluorescent tube 626 is the light-transmitting area 667. The material of the light-transmitting area 667 is transparent. The transparent material may be quartz or plastic.

Preferably, the transparent material is glass. Using glass as the transparent material may avoid the problems of plastic aging and reduction of light transmittance, ensuring the transparency of the transparent material.

Preferably, the transparent material is quartz glass. Quartz glass may enable the lamp cover to maintain a high light transmittance, thus ensuring an efficient germicidal effect.

In this embodiment, the light-transmitting area 667 is located at a central portion of the end wall 665. The light-transmitting area 667 is concave relative to an outer surface of the end wall 665. A light-emitting surface of the light-transmitting 667 of the lamp cover 66 is provided with a laminating film 661. The laminating film 661 covers the transparent material of the lamp cover.

The laminating film 661 is a removable and replaceable laminating film. As a surface of the lamp cover 66 of the UV lamp assembly 60 often undergoes curing reactions in the pool, the surface of the lamp cover 66 will harden and absorb a layer of impurities over a long period, thereby reducing the transmittance of Ultraviolet rays and affecting the germicidal efficiency. The configuration of the laminating film 661 is conducive to isolating impurities. During use, the laminating film 661 can be replaced regularly, i.e., removing the old laminating film and apply a new one, for easy maintenance. In this way, the change of the light transmittance of the light-transmitting area of the lamp cover may be reduced, thereby ensuring the germicidal effect.

Further, when the transparent material of the lamp cover is glass (including both ordinary glass and quartz glass), since the laminating film 661 is disposed on the light-emitting surface of the light-transmitting area 667 of the lamp cover 66 and the laminating film may be adhered to the glass, it can prevent the danger of glass shards falling into the pool due to collisions on the lamp cover. Therefore, the safety is enhanced during using the pool-cleaning robot.

Figure 8:
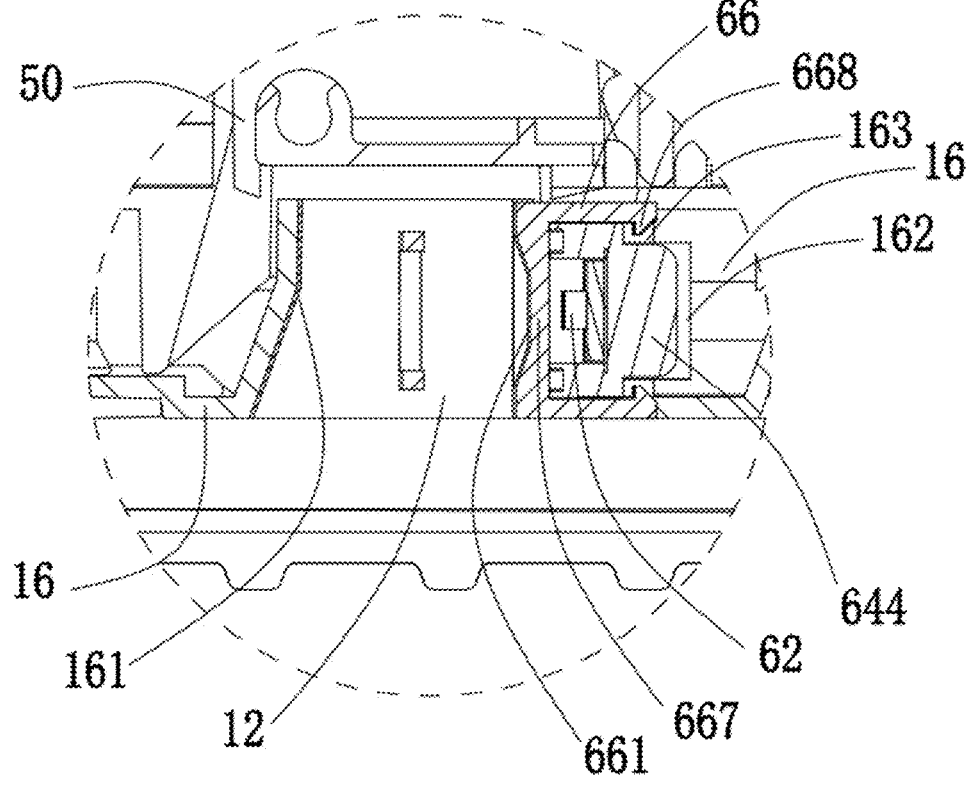
FIG. 8 is an enlarged view of a circled portion in FIG. 7.
Figure 9:
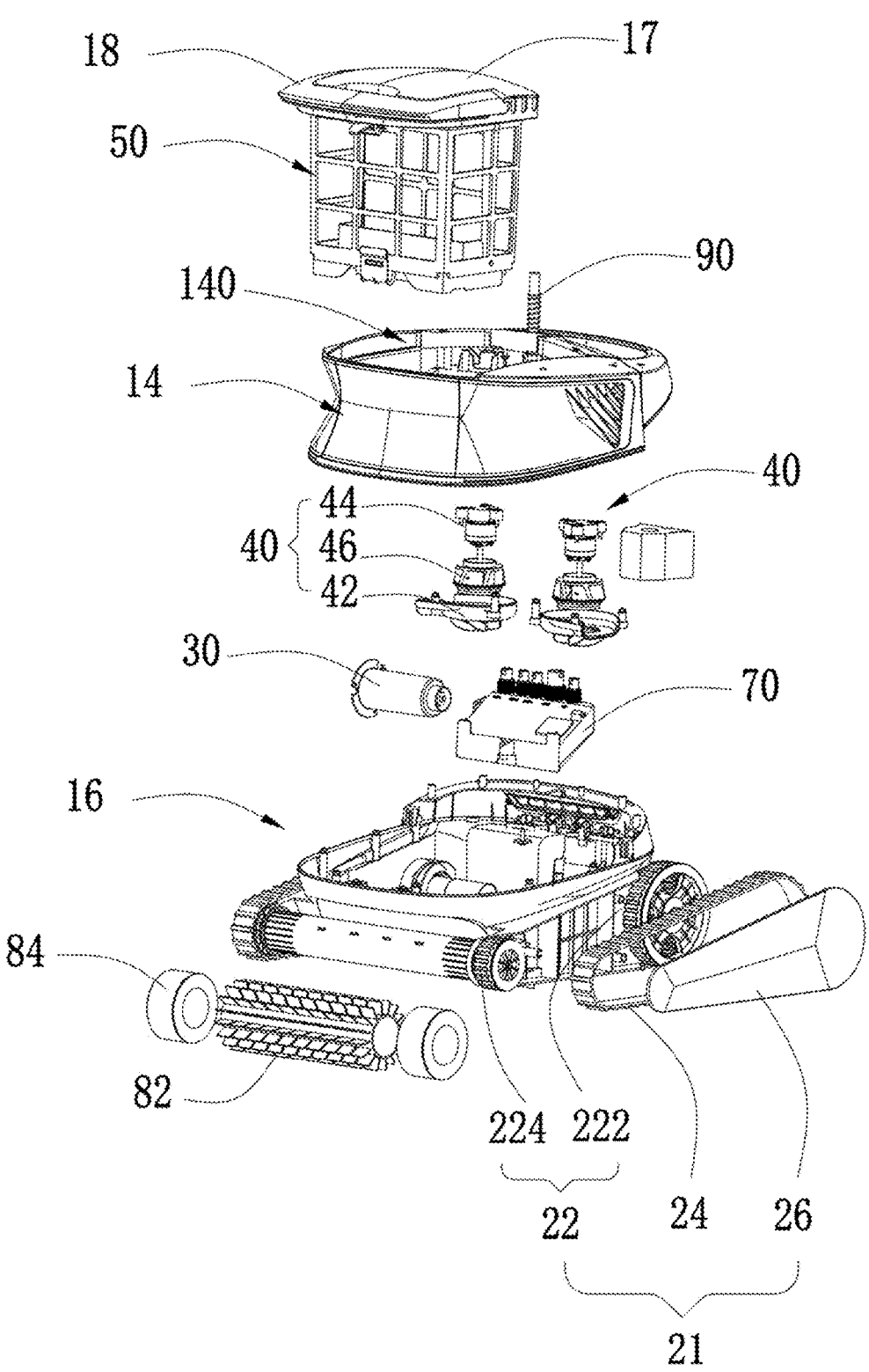
FIG. 9 is an exploded perspective view of a pool-cleaning robot according to a second embodiment of the present disclosure.
Figure 10:
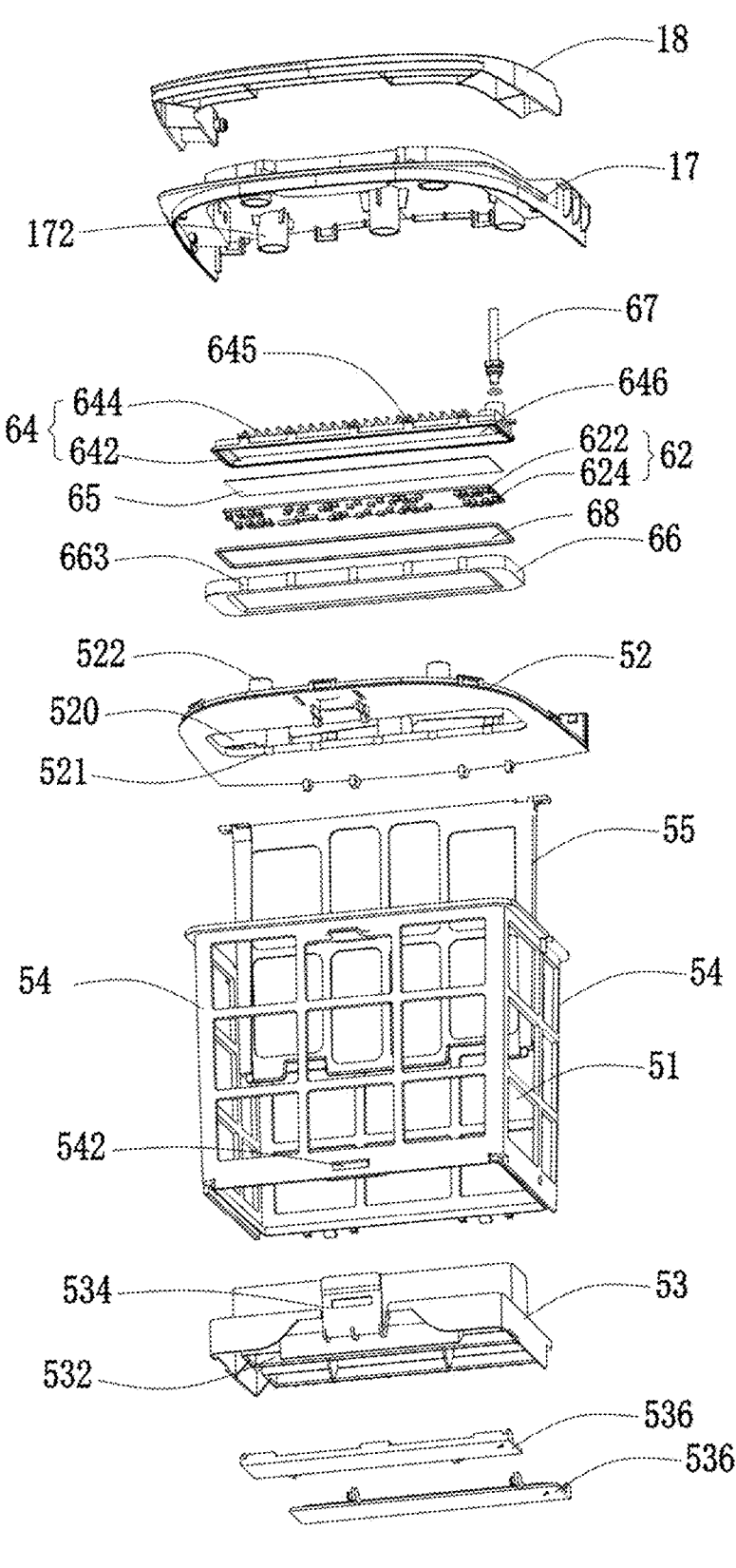
FIG. 10 is a three-dimensional exploded view of a filter assembly and a germicidal lamp assembly of the pool-cleaning robot shown in FIG. 9.
Figure 11:
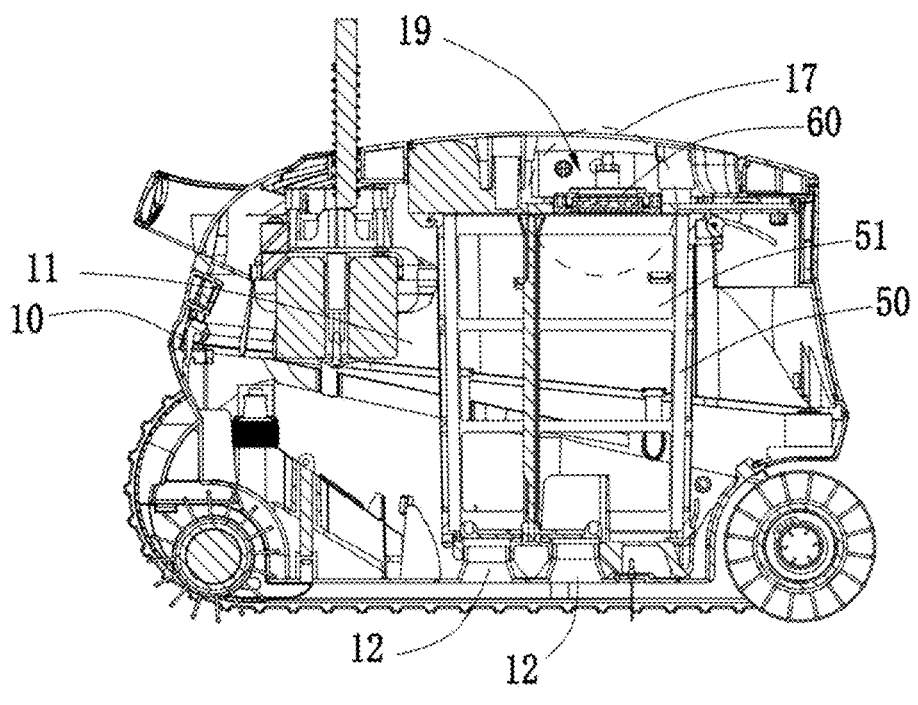
FIG. 11 is a cross-sectional view of the pool-cleaning robot shown in FIG. 9 being in an assembled state.
Figure 12:
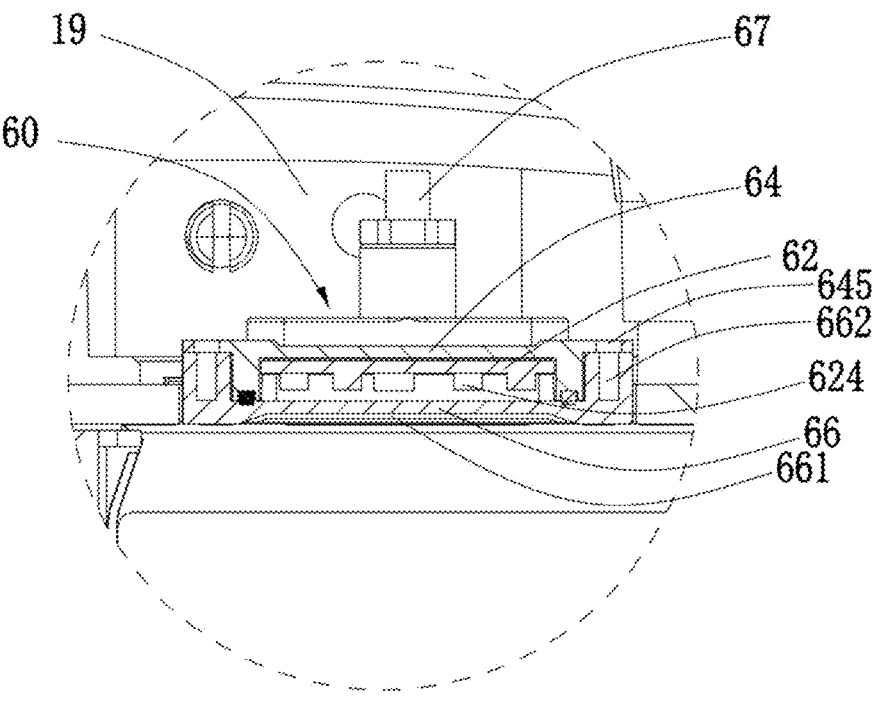
FIG. 12 is an enlarged view of a circled portion in FIG. 11.

In this embodiment, referring to FIG. 8, the germicidal lamp assembly 60 is installed on the housing 10 through a snap connection. The inner wall of the water inlet 12 of the housing 10 defines a slot 163, and an end of the side wall 666 of the lamp cover 66 of the germicidal lamp assembly 60 is provided with a hook 668, which protrudes from the heat-dissipating seat 64. The hook 668 is engaged in the slot of the housing 10, thereby allowing the germicidal lamp assembly 60 to be securely mounted within the flow channel of the water inlet 12. Preferably, the inner wall of the housing 10 further defines a groove 162. When the germicidal lamp assembly 60 is snapped onto the housing 10, the heat-dissipating fins 644 protruding from the germicidal lamp assembly 60 are received in the groove 162 of the housing 10. Preferably, a reflective material 161 is provided on the other side wall of the water inlet 12 opposite to the germicidal lamp assembly 60. On the one hand, the germicidal effect can be enhanced, and on the other hand, in the case where the housing is made of plastic, the housing 10 can be safeguarded from aging by the long-term irradiation of the germicidal lamp assembly 60. The reflective material 161 may be a reflective layer directly coated on a bottom wall, or may be a reflective film, reflective paper or reflective sheet additionally arranged on the side wall, e.g., tin foil.

Continuing to refer to FIGS. 1 to 8, in this embodiment, the housing 10 is composed of an upper housing 14 and a lower housing 16 connected one another, with the receiving chamber 11 defined between the upper housing 14 and the lower housing 16. The water inlet 12 is defined at a bottom of the lower housing 16, and the water outlet 13 is defined on the upper housing 14. The water inlets 12 and two water outlets 13 are each furnished with two. In this embodiment, a number of water inlets 12 is two, and correspondingly, a number of germicidal lamp assemblies 60 is also two. The two germicidal lamp assemblies 60 are respectively disposed at the two water inlets 12. Specifically, in this embodiment, the two germicidal lamp assemblies 60 are installed on side walls of the same side of the two water inlets 12, that is, the two germicidal lamp assemblies 60 are disposed in parallel, and irradiation directions of the two germicidal lamp assemblies 60 are identical in this embodiment. It can be understood that, as an alternative solution, the two germicidal lamp assemblies 60 may also be disposed on the side wall adjacent to the two water inlets 12, and the irradiation directions of the two germicidal lamp assemblies 60 are opposite.

In other embodiments, the two germicidal lamp assemblies 60 may also be disposed around an outer periphery of the water inlet 12. That is, the two germicidal lamp assemblies 60 are arranged at intervals, with the two water inlets 12 located between the two germicidal lamp assemblies 60. The two germicidal lamp assemblies 60 are adjacent to each other and directly facing the bottom of the filter assembly 50, and upwardly irradiate the surface of the filter assembly 50 from the bottom.

The pump assembly 40 is arranged in a flow channel of the receiving chamber 11. The pump assembly 40 includes a pump casing 42, a pump motor 44 and an impeller 46. Driven by the pump motor 44, the impeller 46 drives the water flowing in from the water inlet 12, and then out from the water outlet 13 after passing through the flow channel. The filter assembly 50 is arranged in the flow channel between the water inlet 12 and the water outlet 13. The filter assembly 50 may include a filter paper, a gauze, a filter screen or other filter components, to filter the water entering from the water inlet 12 and then discharge it to the outlet 13, thereby discharging the filtered water from the water outlet 13.

In some embodiments, the motor of the driving assembly 30 may be integrated with the pump motor 44, or the driving assembly 30 may be simultaneously used to drive the pump, that is, the driving assembly 30 has a plurality of output shafts for respectively connecting and driving the wheelset and the impeller of the pump assembly.

The receiving chamber 11 of the housing 10 is further provided with a control device 70. The control device 70 includes a sealed control box, as well as a power module and a control module which are arranged within the control box. In this embodiment, the pool-cleaning robot 100, which is cable-powered, includes a power supply connection cable 90. The power supply connection cable 90 connects the onshore power supply with the power module of the control device 70. In other embodiments, the pool-cleaning robot 100 may also employ a wireless power supply. In the wireless power supply embodiment, the power module includes a rechargeable battery.

The control device 70 is electrically connected to the pump assembly 40 and the power assembly 20 for supplying power to the pump assembly 40 and the power assembly 20. In this embodiment, the control device 70 is electrically connected to the drive assembly 30 to supply power thereto, and controls the movement of the walking assembly 21 through the drive assembly 30, thereby controlling the direction of movement, speed, and the like of the pool-cleaning robot 100. In some embodiments, it is also possible to assist the movement or steering of the body by means of the flow ejection caused by the flow guiding of the pump assembly 40. The control device 70 is also electrically connected to the germicidal lamp assembly 60 to power or control it.

Specifically, in this embodiment, the wheelset 22 of the traveling assembly 21 includes a pair of driving wheels 222 and a pair of driven wheels 224. The traveling assembly 21 further includes two crawler tracks 24 connecting the driving wheel 222 and the driven wheel 224. Each crawler track 24 is connected to a driving wheel 222 and a corresponding driven wheel 224. The driving wheels 222 are driven to rotate by the driving assembly 30, and the driven wheels 224 are driven to rotate synchronously through the crawler tracks 24, thereby achieving the movement of the pool-cleaning robot 100. Preferably, in this embodiment, there is also a side plate 26 configured to cover the walking assembly 21.

Preferably, in this embodiment, at least one roller brush 80 is further provided, which is substantially cylindrical, with a plurality of brush blades 82 disposed on its periphery. The roller brush 80 may be mounted around a wheel axle between the two driving wheels 222 and/or between the two driven wheels 224. In this way, when the pool-cleaning robot 100 moves, the roller brush 80 is driven to rotate, and the trash debris at the bottom of the pool is cleaned synchronously by the brush blades 82.

Preferably, the roller brush 80 further includes sleeves 84 located at both axial ends thereof. The sleeves 84 are preferably made of an anti-slip material (e.g. a sponge) to increase the friction and adhesion between the roller brush 80 and the pool wall and improve the rotation stability of the roller brush 80.

As an alternative embodiment, the power assembly 20 may also include a plurality of thrusters. The plurality of thrusters may include at least one first thruster for driving the pool-cleaning machine 100 to move forwardly, at least one second thruster for driving the pool-cleaning robot 100 to turn left, and at least one third thruster for driving the pool-cleaning robot 100 to turn right. Movements and steering of the pool-cleaning robot 100 within the pool may likewise be achieved by employing the plurality of thrusters. Preferably, the power assembly 20 may also include at least one fourth thruster for driving the pool-cleaning robot 100 to move backwardly.

Preferably, a top of the upper housing 14 has an opening 140. A top cover 17 covers the opening 140 and is openable to expose the opening 140. The filter assembly 50 is detachably installed in the receiving chamber 11. During installation or maintenance, the filter assembly 50 can be put in or taken out through the opening 140. The configuration of the opening 140 makes it convenient to disassemble and clean the filter assembly 50, or to replace the filter screen.

Specifically referring to FIG. 5, in this embodiment, the filter assembly 50 is a basket filter device, which has a top plate 52, a bottom plate 53 and a side wall 54 connecting the top plate 52 and the bottom plate 53. The top plate 52, the bottom plate 53 and the side walls 54 together define the filter chamber 51. The side wall 54 is made as a perimeter-enclosed filter screen. The side wall 54 is substantially enclosed in a rectangular shape with openings at upper and lower ends. The top plate 52 is connected to the upper end of the side wall 54 and covers the upper opening. The bottom plate 53 is connected to the lower end of the side wall 54 and covers the lower opening. The top plate 52 and the bottom plate 53 are detachably connected to the side wall 54, for example, by a snap connection, or by a screw connection. Specifically, in this embodiment, a block or hook 542 is provided at a periphery of a bottom of the side wall 54, and a periphery of the bottom plate 53 extends towards the side wall 54 to form a connecting portion 534, which defines a snapping hole corresponding to the block or hook 542. The snapping hole matches with the block or hook 542 to achieve the snap connection between the side wall 54 and the bottom plate 53. The top plate 52 and the side wall 54 may also connected through the same or similar snap connection, which will not be further described here.

In this embodiment, the top plate 52 of the filter assembly 50 is fixedly connected to the top cover 17 of the housing 10. Preferably, the top cover 17 is also connected with a handle 18. In other embodiments, the top cover 17 is rotatably connected to the upper housing 14 and is reversible relative to the upper housing 14 to open or cover the opening 140. In this case, the filter assembly 50 is either removably connected or not fixedly connected to the top cover 17, allowing the filtration assembly 50 to be easily accessed by opening the top cover 17. In some embodiments, opposing surfaces of the top plate 52 of the filter assembly 50 and the top cover 17 are provided with positioning structures cooperating with each other. Specifically, a first positioning portion 522 is provided on a surface (i.e. an upper surface) of the top plate 52 facing the top cover 17, and a second positioning portion 172 is provided on a surface (i.e. a lower surface) of the top cover 17 facing the top plate 52. The first positioning portion 522 and the second positioning portion 172 cooperate with each other to allow for positional alignment of the top plate 52 and the top cover 17 before installation. Preferably, the first positioning portion 522 of the top plate 52 is a first protruding post, and the second positioning portion 172 of the top cover is a second protruding post with a positioning hole. When the top plate 52 is positionally aligned with the top cover 17, a tip of the first protruding post is engaged in the positioning hole of the second protruding post.

A bottom end of the filter assembly 50 detachably abuts against an inner wall of the lower housing 16. The bottom plate 53 of the filter assembly 50 defines an inlet 532 at a position corresponding to the water inlet 12 of the housing 10. Preferably, a shape and size of the inlet 532 match those of the water inlet 12. The bottom plate 53 further includes a bottom cover 536 pivotally openable to cover the inlet 532. In this embodiment, the two water inlets 12 of the housing 10 include a main water inlet 12 and an auxiliary water inlet 12. The main water inlet 12 is open when working, while the auxiliary water inlet 12 is closed. The bottom cover 536 corresponding to the auxiliary water inlet 12 is provided with a counterweight. When the pool-cleaning robot 100 climbs the wall, the bottom cover 536 at the auxiliary water inlet 12 opens under the action of gravity, thereby opening the auxiliary water inlet 12. That is, when the pool-cleaning robot 100 climbs the wall, the two water inlets 12 are both open. This increases the water flowing into the flow channel, which in turn increases the water flowing out of the water outlet 13 as well as increasing the counterthrust force, allowing the pool-cleaning robot 100 to securely adhere to the wall of the pool for cleaning under the counterthrust force.

Preferably, the filter assembly 50 further includes a middle partition 55 located in the filter chamber 51. The middle partition 55 is located at a central portion of the filter chamber 51, dividing the filter chamber 51 in half. A top end of the middle partition 55 abuts against the top plate 52, and a bottom end of the middle partition 55 abuts against the bottom plate 53. The configuration of the middle partition 55 is conducive to enhancing the filtering effect.

The germicidal lamp assembly 60 is electrically connected to the control device 70 so as to be powered and controlled by the control device 70. The germicidal lamp assembly 60 is therefore preferably fixedly mounted in the housing 10. The germicidal lamp assembly 60 further includes a power supply cable 67 electrically connected to the light source module 62. The power supply cable 67 may be arranged along the inner wall of the housing 10 and signal connected to the control mainboard within the control device 70 for power supply and control.

When the above pool-cleaning robot 100 is in use, the housing 10 walks in the pool through the walking assembly 21 and its internal driving assembly 30. Under the action of the pump assembly 40, the pool water enters the filter assembly 50 from the water inlet 12, and is discharged from the water outlet 13 after being filtered through the filter screen, achieving the objective of cleaning the pool water. In this process, the germicidal lamp assembly 60 irradiates the water in the flow channel of the water inlet 12 throughout, to sterilize and disinfect the water after entering the housing 10 but before filtration, which prevents bacterial contaminants carried in the water from accumulating on the filter assembly 50 and causing secondary pollution to the water.

Additionally, it also prevents the generation of odor due to excessive bacteria inside the filter assembly 50, decreasing the frequency of cleaning and replacing the filter assembly 50, and greatly improving the customer experience.

In this embodiment, the pool-cleaning robot 100 is cable-powered, which allows the use of high-power germicidal lamps for long-term operation. This ensures that when the high-speed flowing water is sterilized during operation, bacteria in the water can be effectively eliminated, ensuring the germicidal effect.

On the other hand, a pool-cleaning robot generally follows an electronic control box for power supply or a buoy for enhanced communication. The buoy floats on the water, and a germicidal lamp assembly 60 may be provided at a bottom of the buoy to sterilize and disinfect a portion of the water.

FIGS. 9-12 illustrate a pool-cleaning robot according to a second embodiment of the present disclosure. This embodiment is similar to the first embodiment, except for the position of the germicidal lamp assembly 60. In this embodiment, there is only one germicidal lamp assembly 60 provided, and the germicidal lamp assembly 60 is disposed on an inner wall of a top cover 17 of a housing 10. In addition, the structure of the germicidal lamp assembly 60 of this embodiment is also slightly altered.

Similar to the above embodiment, the germicidal lamp assembly 60 of this embodiment also includes a light source module 62, a heat-dissipating seat 64 and a lamp cover 66. The heat-dissipating seat 64 includes a base 642 and a plurality of heat-dissipating fins 644 provided on an upper side surface of the base 642. The light source module 62 is fixed on an underside of the base 642 of the heat-dissipating seat 64. The light source module 62 includes a light-emitting element. The light-emitting element includes a fluorescent tube. Alternatively, the light source module 62 includes a substrate 622 and a plurality of lamp beads 624 disposed on the substrate 622. The lamp beads 624 are used to emit Ultraviolet rays. The substrate 622 is attached to a lower surface of the base 642. The lamp beads 624 are disposed on a side of the substrate 622 facing away from the base 642. Connecting surfaces between the substrate 622 and the base 642 are coated with thermal conductive paste 65, which is beneficial for quickly conducting the heat from the substrate 622 to the base 642 of the heat-dissipating seat 64, and then dissipating the heat through the heat-dissipating fins 644. The lamp cover 66 is connected to the base 642 of the heat-dissipating seat 64 for enclosing the light source module 62 inside, to protect a circuit of the light source module 62. Preferably, a sealing ring 68 is provided between the lamp cover 66 and the lower surface of the base 642 to seal the light source module 62 and prevent water seepage from damaging the circuit of the light source module 62 during underwater operation.

Preferably, a bottom surface of the base 642 is recessed inwardly to form an accommodation cavity 646, and the light source module 62 is received in the accommodation cavity 646. A perimeter of the lamp cover 66 is connected to a bottom perimeter of the base 642, thereby enclosing the accommodation cavity 646 of the base 642, as well as sealing the accommodation cavity 646 through the sealing ring 68.

Similar to the above embodiment, in this embodiment, an area of the lamp cover 66 corresponding to the light-emitting area of the light source module 62 is a light-transmitting area 667. Specifically, an area of the lamp cover 66 corresponding to the lamp beads 624 of the light source module 62 is the light-transmitting area 667; or an area of the lamp cover 66 corresponding to the fluorescent tube 626 of the light source module 62 is the light-transmitting area 667. The material of the light-transmitting area 667 is transparent. The transparent material may be quartz or plastic.

Preferably, the transparent material is glass. Using glass as the transparent material may avoid the problems of plastic aging and reduction of light transmittance, ensuring the transparency of the material.

Preferably, the transparent material is quartz glass. Quartz glass may enable the lamp cover to maintain a high light transmittance, thus ensuring an efficient germicidal effect.

A light-emitting surface of the light-transmitting area 667 of the lamp cover 66 is provided with a laminating film 661, which covers the transparent material of the lamp cover.

The difference between the germicidal lamp assembly 60 of this embodiment and the germicidal lamp assembly 60 of the first embodiment is that, in this embodiment, the germicidal lamp assembly 60 is installed in an installation space 19 between the top plate 52 and the top cover 17.

Preferably, a sealing ring may be provided around a perimeter of the top plate 52 of the filter assembly 50 contacting the top cover 17 to form a sealed connection, thereby sealing the installation space 19.

In some embodiments, the germicidal lamp assembly 60 is embedded in the top plate 52 of the filter assembly 50. Specifically, a perforation 520 is defined at a central portion of the top plate 52 corresponding to the lamp cover 66 of the germicidal lamp assembly 60, in which the lamp cover 66 of the germicidal lamp assembly 60 is engaged. Light from the light source module 62 passes through the lamp cover 66 and then directly irradiates the filter chamber 51 and the filter screen around it after passing through the perforation 520. Preferably, limiting structures are provided between the periphery of the lamp cover 66 and a wall portion of the top plate 52 defining the through hole 520. Specifically, the limiting structures include a limiting protrusion 663 arranged on the periphery of the lamp cover 66 and a limiting groove 521 formed on the wall of the top plate 52, thus, the precise positioning of the lamp cover 66 with the top plate 52 is achieved through the cooperation of the limiting projection 663 and the limiting recess 521.

As an example, the base 642 is connected to the lamp cover 66 through fasteners. Specifically, a peripheral edge of the base 642 defines a plurality of fixing holes 645, and a perimeter of the lamp cover 66 correspondingly defines a plurality of connecting holes 662, which are threaded holes. During installation, the fixing holes 645 of the base 642 are aligned with the connecting holes 662 of the lamp cover 66, and the fasteners (such as bolts and screws) may be passed through the fixing holes 645 and threadedly connected to the connecting holes 662 to achieve the assembly of the germicidal lamp assembly 60.

In this embodiment, the top cover 17 is relatively fixedly connected to the top plate 52 of the filter assembly 50. In other embodiments, instead of being connected with the top plate 52 of the filter assembly 50, the top cover 17 may be rotatably connected to the upper housing 14 on one side so that it is reversible to open or close the opening. In this case, the germicidal lamp assembly 60 is preferably fixed relative to the top cover 17, that is, the germicidal lamp assembly 60 is fixedly connected to the inner side of the top cover 17 for easy wiring.

In the pool-cleaning robot of the embodiment of the present disclosure, since the filter screen is usually not completely vertical, and on the other hand, dirt is also accumulated at a bottom of the filter assembly 50, the light source module 62 can directly irradiate the filter screen and surface of the dirt. The objective of germicidal and disinfection can be fully achieved.

When the above pool-cleaning robot 100 is in use, the housing 10 walks in the pool through the walking assembly 21 and its internal driving assembly 30. Under the action of the pump assembly 40, the water in the pool enters the filter assembly 50 from the water inlet 12, and is discharged from the water outlet 13 after being filtered through the filter screen, to achieve the objective of cleaning the pool water. In this process, the germicidal lamp assembly 60 irradiates the filter screen and the surface of the dirt throughout, to sterilize and disinfect the filter assembly and the water being filtered by the filter assembly, which prevents secondary pollution to the water. At the same time, it also prevents the generation of odor due to excessive bacteria inside the filter assembly 50, reducing the frequency of cleaning and replacing the filter assembly 50, and greatly improving the customer experience.

Other components of this embodiment are the same as those of the first embodiment. For details, please refer to the above-detailed description of the first embodiment, which will not be described again here.

In other embodiments, the germicidal lamp assembly 60 is arranged on the inner surface of the side wall of the housing 10. The germicidal lamp assembly 60 is adjacent to and directly opposite to the side wall 54 of the filter assembly 50. The germicidal lamp assembly 60 directly irradiates the side wall of the filter assembly 50.

In the above described embodiments, the filter assemblies 50 are all basket filter devices. As an alternative, filter elements in the form of filter cores, specifically cylindrical filter cores, may also be employed. The germicidal lamp assembly 60 may employ a circular ring-shaped germicidal fluorescent tube. The ring-shaped germicidal fluorescent tube is arranged around an outer periphery of the water inlet 12, thus directly irradiating the bottom of the filter assembly 50; alternatively, the germicidal lamp assembly 60 may also be disposed at the top of the filter assembly 50, specifically on an inner wall of a top cover, facing a top of the filter assembly 50, with the germicidal lamp assembly 60 directly irradiating the top of the filter assembly.

In the first embodiment, the laminating film 661 is a removable and replaceable laminating film. In other embodiments, referring to the underwater germicidal lamp assembly shown in FIGS. 13-15, the laminating film 661 is non-removably disposed on the light-emitting surface of the light-transmitting area of the lamp cover. The permanently attached laminating film 661 may reduce the problem of a surface of the lamp cover of the underwater germicidal lamp hardening and adsorbing a layer of impurities due to long-term operation in the prior art, thus avoiding decreasing a light transmittance caused by chemical reactions between the lamp cover and impurities. In this way, the light transmittance of the light-transmitting area of the lamp cover may be maintained, thus ensuring the germicidal effect. Moreover, since the chemical reaction between the lamp cover and impurities is avoided, the service life of the germicidal lamp assembly may be effectively improved.

Preferably, the laminating film 661 is made of a material with high transparency and low adsorption properties. The lamp cover may maintain a high light transmittance by employing a material with high transparency. Further, due to the low adsorption property, the surface of the laminating film 661, i.e. the surface of the lamp cover, is not prone to adsorbing impurities. The surface of the lamp cover 66 is prevented from adhering impurities with long period use even without replacing the laminating film 661, thereby making it convenient to use and ensure the germicidal efficiency.

Preferably, the laminating film 661 contains material of ETFE (ethylene-tetra-fluoro-ethylene copolymer) or FEP (fluorinated ethylene propylene). Preferably, the laminating film 661 is an FEP film or an ETFE film.

Wherein, the material of ETFE is a type of durable and lightweight fluoroplastic material, which has excellent chemical resistance, weather resistance, and high light transmittance. The ETFE has main features of: strong resistance to ultraviolet rays and weather, maintaining stable performance even under long period sunlight exposure and harsh conditions; high light transmittance, making it very suitable for applications such as greenhouses and skylights where light transmission is required; self-cleaning ability, with a smooth surface that is not easy to get dirty; chemical corrosion resistance, suitable for applications in chemical environments; lightweight and high strength, lighter than traditional glass but with higher impact resistance; and high-temperature resistance, maintaining physical properties within a wide temperature range.

Wherein, FEP film is a thin film made of fluoroplastic, which has excellent chemical resistance and electrical insulation properties. The characteristics of FEP film are similar to PTFE (polytetrafluoroethylene), but it has better processability and transparency. The PEP has main features of: outstanding chemical resistance, FEP has extremely strong corrosion resistance to most chemicals. High-temperature stability, FEP film can maintain its performance unchanged within a wide temperature range of −200° C. to +200° C. High transparency, compared with other fluoroplastics, FEP film is more transparent. Excellent electrical insulation, FEP film has a very low dielectric constant and good electrical insulation properties. Low friction coefficient, the surface is very smooth, with self-lubricating properties, and is not prone to adhering to impurities. UV resistance: FEP film has extremely strong resistance to ultraviolet rays when exposed outdoors.

Therefore, the laminating film made of the material of ETFE or FEP may maintain a high light transmittance. Further, due to the surface of the laminating film made of ETFE or FEP is not prone to adsorbing impurities, the surface of the lamp cover 66 is prevented from adhering impurities even without replacing the laminating film and even use for a long period time, thereby making it convenient to use and ensure the germicidal efficiency.

Figure 16:
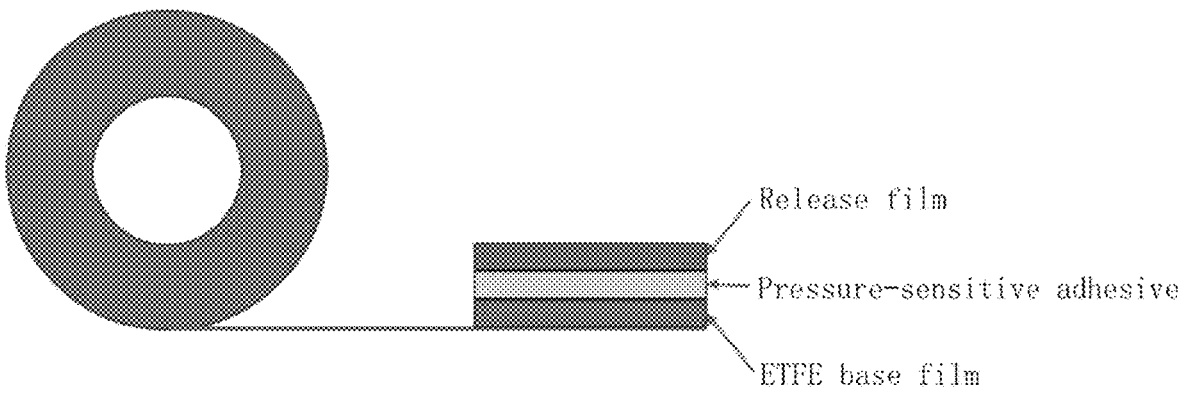
FIG. 16 is a schematic view of a laminating film of a germicidal lamp assembly according to an embodiment of the present disclosure, wherein the laminating film is preferably made of ETFE tape.

Preferably, referring to FIG. 16, the laminating film 661 is an ETFE tape. The ETFE tape may include an ETFE base film, a pressure-sensitive adhesive, and a release film stacked in sequence. Wherein, the release film is a type of film used to prevent sticky materials (such as pressure-sensitive adhesives, tapes, adhesives, etc.) from adhering when the laminating film 661 is not used. The release film has a specially treated surface and provides excellent anti-adhesive properties, enabling it easily separated from sticky materials without affecting the performance of the materials or leaving any residue. The release film may be made of plastic substrates (such as PET, PE, PP, etc.) and is preferably coated with a layer of release agent like silicone oil or fluorinated compounds. Pressure-sensitive adhesive (PSA) is an adhesive that can be adhered under slight pressure. Pressure-sensitive adhesive may exert stickiness to firmly attach to a variety of surfaces without being heated, solvents, or water. Pressure-sensitive adhesive has unique features, providing long-lasting adhesion and may be removed or re-adhered as needed. The composition of Pressure-sensitive adhesive may include elastomers and resins, which provide good adhesion, flexibility, and durability.

Specifically, the performance of ETFE tape is shown in the following Table 1.

TABLE 1

| Conventional performance | | | |
| --- | --- | --- | --- |
| Items | Testing methods | Unit | Typical value |
| Thickness of the substrate of the tape | ISO 4593 | μm | 100 |
| Thickness of adhesive layer | ISO 4593 | μm | 50 |
| Transmittance of visible light | ASTM D1003 | % | 92 |
| Adhesive strength (with ETFE) | ASTM D1876 | N/25 mm | 8 |
| Adhesive strength (with stainless steel) | ASTM D903 | N/25 mm | 8 |
| Adhesive strength (with glass) | ASTM D903 | N/25 mm | 8 |
| Ultimate tensile strength | ISO 527-3 | MPa | 50 |
| Elongation at break | ISO 527-3 | % | 350 |
| Tensile strength at 10% strain | ISO 527-3 | MPa | 18 |
| Tear strength | DIN 53363 | N/mm | 400 |
| Long-term service temperature | UL 746-B | ° C. | 150 |
| Anti-aging performance | | | |

TABLE 1-continued

| Aging Manners | Testing items | Testing methods | Exposed for 1000 hours | Exposed for 3000 hours | Exposed for 5000 hours |
|---|---|---|---|---|---|
| Hygrothermal aging (85° C./85% RH) | Adhesive strength (with ETFE) | ASTM 1876 | 8.5 | 8.7 | 8.3 |
| | Transmittance of visible light | ASTM D1003 | 92 | 92 | 92 |
| UVB aging (0.76 W at 313 nm) | Adhesive strength (with ETFE) | ASTM 1876 | 8.3 | 8.5 | 8.1 |
| | Transmittance of visible light | ASTM D1003 | 92 | 92 | 92 |

Due to the excellent adhesive properties of ETFE tape, it may be directly adhered to non-stick substrates such as ETFE, FEP, and PFA, which has excellent impact resistance and tear resistance, outstanding chemical resistance, heat resistance, and weather resistance, as well as excellent visible light transmittance and excellent flame retardancy.

Figure 13:
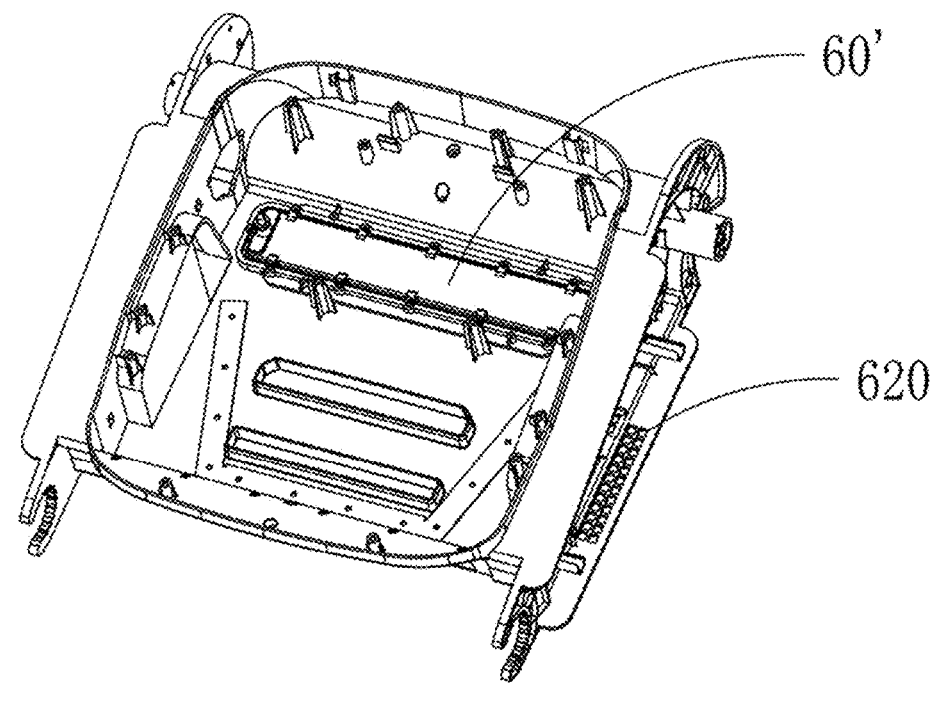
FIG. 13 is a schematic assembled view of a lower housing and a germicidal lamp assembly of a pool-cleaning robot according to another embodiment of the present disclosure.
Figure 14:
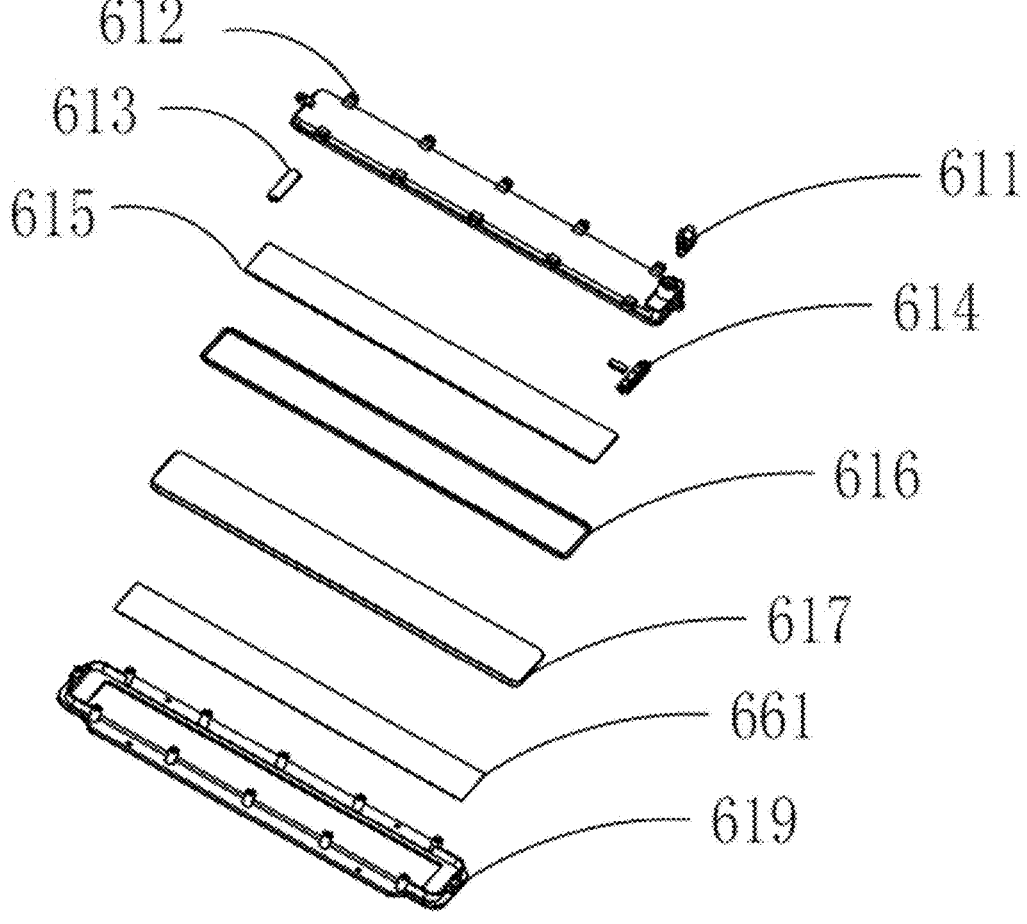
FIG. 14 is an exploded perspective view of the germicidal lamp assembly in FIG. 13.
Figure 15:
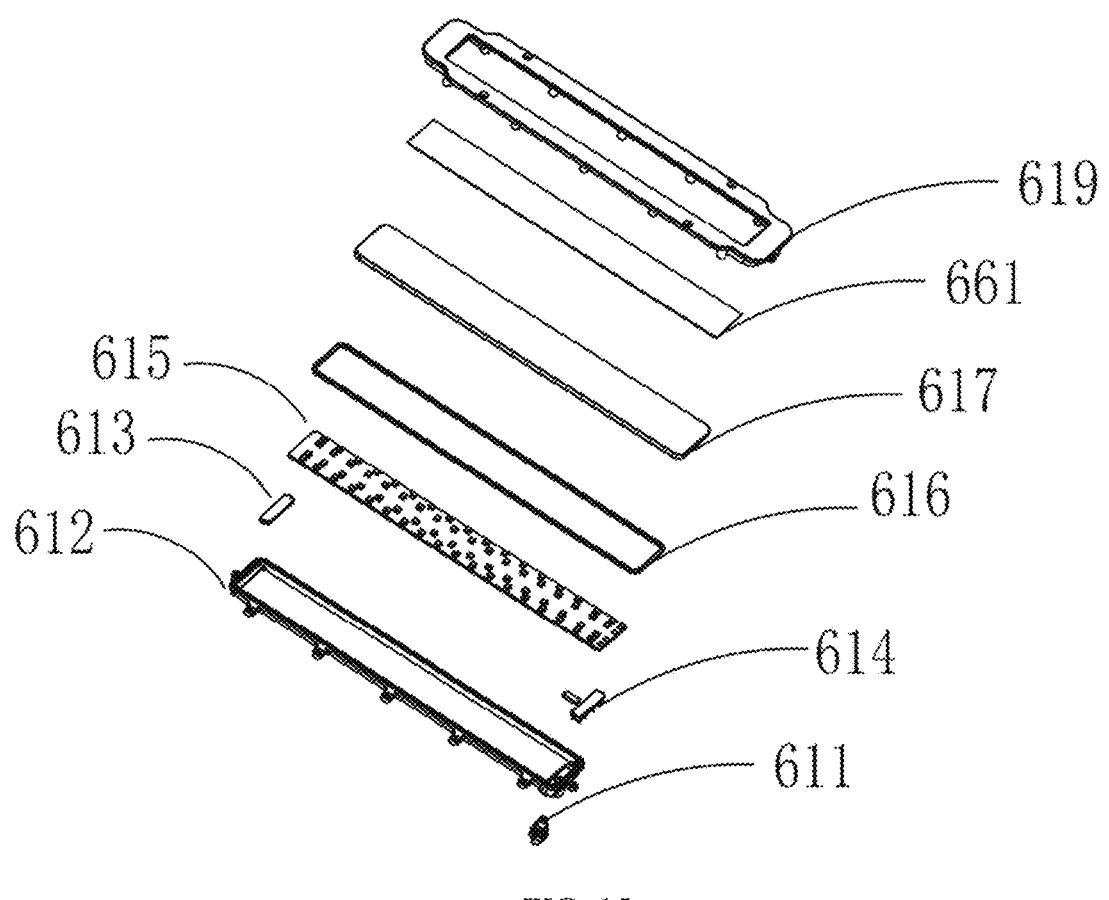
FIG. 15 is a schematic view of the germicidal lamp assembly in FIG. 14 viewed from another angle.

Specifically, referring to FIGS. 13-15, in some embodiments, the germicidal lamp assembly 60 may be assembled to the lower housing 620 of the pool-cleaning robot. In this embodiment, the bottom wall of the lower housing 620 defines a through mounting hole. The germicidal lamp assembly 60' is assembled in the mounting hole, and the light-emitting surface of the germicidal lamp assembly 60' downwardly irradiates the surface of the pool wall from the bottom surface of the lower housing 620.

Specifically, in this embodiment, the germicidal lamp assembly 60' includes: a light source module 615, a base 612, and a lamp cover. The light source module 615 is fixed on one side surface of the base 612. The lamp cover envelops around an outer periphery of the light source module 615, and is connected to the base 612 in a sealed manner.

The light source module 615 of this embodiment can adopt the structure of the light source module of the first embodiment or the second embodiment, which will not be described again here.

In this embodiment, the base 612 differs from the above described embodiments in that the base 612 does not have the heat-dissipating fins.

In addition, in this embodiment, the lamp cover includes a transparent cover plate 617, a connecting frame 619, and a laminating film 661 covering a surface of the transparent cover plate 617. The transparent cover plate 617 is made of a transparent material, preferably glass, and more preferably quartz glass. The connecting frame 619 is a hollow structure with an opening in the middle. A length and a width of the opening are respectively smaller than a length and a width of the transparent cover plate 617. Preferably, the material of the connecting frame 619 is different from that of the transparent cover plate 617.

Similarly to the above described embodiments, a bottom surface of the base 612 is recessed inwardly to form an accommodating cavity. The light source module 615 is received in the accommodating cavity.

Unlike the above described embodiments, in this embodiment, the transparent cover plate 617 is placed over the opening of the accommodating cavity. A perimeter of the connecting frame 619 is connected to a perimeter of the base 612, preferably by fasteners such as screws or snap-fit connections (the connecting manner may adopt the structures of the other above described embodiments, and will not be described again here). Thereby, a perimeter of the transparent cover plate 617 is clamped between the base 612 and the connecting frame 619. A central area of the transparent cover plate 617 is facing the opening of the connecting frame 619 to form a light-transmitting area, allowing the light emitted by the light source module 615 to pass through the transparent cover plate 617 and irradiate the working environment to achieve the germicidal effect. The light-transmitting area of the transparent cover plate 617 is exposed to the water in the pool through the opening.

The laminating film 661 is attached to the light-emitting surface of the transparent cover plate 617. The laminating film 661 may be combined with the transparent cover plate 617 by coating processes or by adhesion. The laminating film 661 is preferably an FEP film or an ETFE film. The advantages and properties of FEP films and ETFE films have been detailed in the preceding text and will not be described again here.

The circuit board of the light source module 615 is integrated with various electronic components, which are used to control a working state of the germicidal lamp assembly. The light source module 615 may be connected to a power supply by electrical connectors, pins, sockets, or conductive wiring, thereby providing power to the germicidal lamp assembly. Specifically, in this embodiment, the light source module 615 is connected to the power supply by conductive terminals 614 and a conductive connector 611. The conductive connector 611 is fixed on the base 612. The conductive terminals 614 electrically connect the circuit board of the light source module 615 with the conductive connector 611, thereby conducting the power supply circuit.

In this embodiment, a spacer 613 is further provided between the light source module 615 and the base 612. Specifically, both the conductive terminal 614 and the spacer 613 are located between the opposite surfaces of the light source module 615 and the base 612. Preferably, the conductive terminal 614 is positioned at one end of the base 612 in the lengthwise direction, and the spacer 613 is positioned at the other end of the base 612 in the lengthwise direction.

Preferably, a sealing ring 616 is provided between the lamp cover and the lower surface of the base 612 to seal the light source module 615 and prevent water seepage from damaging the circuit of the light source module 615 during underwater operation. Preferably, the sealing ring 616 contacts a perimeter of the transparent cover plate 617 and may be connected by a latching groove or adhered with glue. During working of the germicidal lamp assembly, the sealing ring 616 may prevent external dust, moisture, and other impurities from entering into the interior of the lamp, thereby protecting the internal electronic components (such as the printed circuit board assembly of the light source module 615) and the lamp beads from damage.

In one embodiment, the transparent cover plate 617 is made of glass, and the laminating film 661 is an FEP film or an ETFE film. This combination, especially the combination of quartz glass with an FEP film or an ETFE film, may perform a high light transmittance and impact resistance.

Specifically, the following are the experimental data obtained from the light transmittance test and drop test conducted based on a laminating film 661' made of the above described ETFE tape.

(1) Light Transmittance Test

Before the experiment, the appearance of the pool-cleaning robot sample was checked, and the light transmittance data was measured. The light transmittance of ordinary single glass is between 28% and 30%. The following Table 2 shows the light transmittance test results obtained from the combination of the laminating film 661 made of ETFE tape and quartz glass.

TABLE 2

| film | glass | Add sample μW/cm² | No sample added μW/cm² | transmittance | Average |
|---|---|---|---|---|---|
| UV transmittance test -0726 (film + glass) | | | | | |
| Name: ETFE | UVC | 1042 | 1306 | 79.79% | 79.84% |
| tape | component | 685 | 857 | 79.93% | |
| | quartz glass | 1173 | 1470 | 79.80% | |
| UV transmittance test -0730(film + glass) | | | | | |
| Has been irradiated at 100% power for 93 hours | | | | | |
| Name: ETFE | UVC | 870 | 1100 | 79.09% | 79.66% |
| tape | component | 512 | 641 | 79.88% | |
| | quartz glass | 1032 | 1290 | 80.00% | |
| UV transmittance test -0807(film + glass) | | | | | |
| Has been irradiated at 100% power for 285 hours | | | | | |
| Name: ETFE | UVC | 997 | 1245 | 80.08% | 80.21% |
| tape | component | 1128 | 1405 | 80.28% | |
| | quartz glass | 667 | 831 | 80.26% | |
| UV transmittance test -0815(film + glass) | | | | | |
| Has been irradiated at 100% power for 478 hours | | | | | |
| Name: ETFE | UVC | 488 | 610 | 80.00% | 79.24% |
| tape | component | 600 | 756 | 79.37% | |
| | quartz glass | 771 | 984 | 78.35 | |

From the above data, it can be seen that the combination of the laminating film 661 made of ETFE tape and quartz glass may maintain a high light transmittance.

(2) Drop Test

Before the experiment, the appearance of the pool-cleaning robot sample (the lamp cover of the germicidal lamp assembly is made of quartz glass) was checked and found to be normal. The bare machine was dropped. The test height was 30 cm, for 10 times; the direction of the drop was according to the actual usage state.

After the test, the appearance of the pool-cleaning robot sample was checked and found to be normal.

From the above tests, it can be seen that when the lamp cover is made of quartz glass, the germicidal lamp assembly of the pool-cleaning robot has good impact resistance and is not prone to breaking, thereby improving the safety of the pool-cleaning robot during using.

Based on the description of the above embodiments, the present disclosure further provides an underwater germicidal lamp assembly, which includes a base, a light source module connected to the base and a lamp cover covering the light source module. The light source module includes a light-emitting element. An area of the lamp cover corresponding to the light-emitting element of the light source module is a light-transmitting area. A light-emitting surface of the light-transmitting area is provided with a laminating film. The laminating film may be permanently set on the light-emitting surface of the light-transmitting area, or removable and replaceable. The structure of the underwater germicidal lamp assembly may be the same as the above described embodiments, and will not be described again here.

Although the present disclosure has been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts or arrangements of the subject combination arrangement within the scope of the disclosure, the drawings and the appended claims. In addition to variations and modifications in the component parts and/or arrangements, alternative uses will also be apparent to those skilled in the art.

The invention claimed is:

1. An underwater germicidal lamp assembly, comprising:
   a base;
   a light source module connected to the base, the light source module comprising a light-emitting element; and
   a lamp cover covering the light source module, an area of the lamp cover corresponding to a light-emitting area of the light source module being a light-transmitting area;
   wherein a light-emitting surface of the light-transmitting area is provided with a laminating film, and the laminating film is a removable laminating film to make the light-transmitting area of the lamp cover having a high light transmittance to ensuring a germicidal effect; and
   a plurality of slits are defined on a perimeter of the lamp cover to enable deforming the perimeter of the lamp cover to expand slightly outwardly during assembly.

2. The underwater germicidal lamp assembly according to claim 1, wherein the laminating film contains material of ETFE or FEP.

3. The underwater germicidal lamp assembly according to claim 1, wherein the light-transmitting area is made of glass.

4. The underwater germicidal lamp assembly according to claim 3, wherein the glass is quartz glass.

5. The underwater germicidal lamp assembly according to claim 1, wherein the light source module further comprises a substrate, and the light-emitting element is a plurality of lamp beads disposed on the substrate.

6. The underwater germicidal lamp assembly according to claim 1, wherein the light-emitting element comprises a fluorescent tube.

7. The underwater germicidal lamp assembly according to claim 1, wherein the light-transmitting area of the lamp cover is recessed inwardly relative to an outer surface of the lamp cover.

8. The underwater germicidal lamp assembly according to claim 1, wherein the base has opposite first and second sides, the light source module is disposed on the first side of the base, and a plurality of heat-dissipating fins are disposed on the second side of the base.

9. The underwater germicidal lamp assembly according to claim 1, wherein an accommodation cavity is formed on a side of the base disposing the light source module, the light source module is received in the accommodation cavity, and the lamp cover is connected to the base in a sealed manner thereby sealing the accommodation cavity.

10. The underwater germicidal lamp assembly according to claim 1, wherein the lamp cover is snapped on a periphery of the base, or the lamp cover and the base are connected by a fastener.

11. A pool-cleaning robot, comprising:

a housing, defining a receiving chamber therein and a water inlet and a water outlet which are fluidly communicated with one another;

a power assembly, connected to the housing and configured to provide power to drive the pool-cleaning robot to travel in a pool;

a filter assembly, arranged in the receiving chamber and having a filter chamber that is in fluid communication with the water inlet and the water outlet;

a pump assembly, arranged in the receiving chamber and configured to drive the water flowing into the receiving chamber from the water inlet and then out from the water outlet after being filtered by the filter assembly; and an underwater germicidal lamp assembly comprising:

a base;

a light source module connected to the base, the light source module comprising a light-emitting element; and a lamp cover covering the light source module, an area of the lamp cover corresponding to a light-emitting area of the light source assembly being a light-transmitting area;

wherein a light-emitting surface of the light-transmitting area is provided with a laminating film, and the laminating film is a removable laminating film to make the light-transmitting area of the lamp cover having a high light transmittance to ensuring a germicidal effect; the germicidal lamp assembly further comprises a heat-dissipating seat, and a plurality of heat-dissipating fins are provided on an upper side surface of the base;

an inner wall of the water inlet of the housing defines a slot, and an end of an side wall of the lamp cover of the germicidal lamp assembly is provided with a hook, which protrudes from the heat-dissipating seat, the hook is engaged in the slot of the housing, thereby allowing the germicidal lamp assembly to be securely mounted within the flow channel of the water inlet; and an inner wall of the housing further defines a groove, when the germicidal lamp assembly is snapped onto the housing, the heat-dissipating fins protruding from the germicidal lamp assembly are received in the groove of the housing.

12. The pool-cleaning robot according to claim 11, wherein the germicidal lamp assembly is arranged on an outer wall of the housing or inside the housing.

13. The pool-cleaning robot according to claim 12, wherein the germicidal lamp assembly is arranged in the receiving chamber, and located above, below and/or at a side of the filter assembly.

14. The pool-cleaning robot according to claim 12, wherein the germicidal lamp assembly is arranged on a side wall of a flow channel of the water inlet to irradiate the flow channel of the water inlet.

15. The pool-cleaning robot according to claim 14, wherein a shape of the germicidal lamp assembly is substantially adapted to a shape of the water inlet.

16. The pool-cleaning robot according to claim 11, wherein the light source module further comprises a substrate, and the light-emitting element is a plurality of lamp beads disposed on the substrate; or the light-emitting element comprises a fluorescent tube.

17. The pool-cleaning robot according to claim 11, wherein the light-transmitting area of the lamp cover is recessed inwardly relative to an outer surface of the lamp cover.

18. A pool-cleaning robot, comprising:

a housing, defining a receiving chamber therein and a water inlet and a water outlet which are fluidly communicated with one another;

a power assembly, connected to the housing and configured to provide power to drive the pool-cleaning robot to travel in a pool;

a filter assembly, arranged in the receiving chamber and having a filter chamber that is in fluid communication with the water inlet and the water outlet;

a pump assembly, arranged in the receiving chamber and configured to drive the water flowing into the receiving chamber from the water inlet and then out from the water outlet after being filtered by the filter assembly; and an underwater germicidal lamp assembly comprising:

a base;

a light source module connected to the base, the light source module comprising a light-emitting element; and a lamp cover covering the light source module, an area of the lamp cover corresponding to a light-emitting area of the light source assembly being a light-transmitting area;

wherein a light-emitting surface of the light-transmitting area is provided with a laminating film, the water inlet serves as a main water inlet and the housing defines an auxiliary water inlet, the filter assembly is a basket filter device having a top plate, a bottom plate and a side wall connecting the top plate and the bottom plate, the bottom plate of the filter assembly defines an inlet at a position corresponding to the water inlet of the housing, the bottom plate further comprises a bottom cover pivotally openable to cover the inlet, the bottom cover corresponding to the auxiliary water inlet is provided with a counterweight.

* * * * *